United States Patent [19]

Coker et al.

[11] Patent Number: 4,610,995

[45] Date of Patent: Sep. 9, 1986

[54] CERTAIN 1,1-DIARYL-PROPENYL-3-(1-PYRROLIDINO-2-CARBOXYLIC ACIDS, DERIVATIVES THEREOF AND THEIR ANTI-HISTAMINIC PROPERTIES

[76] Inventors: Geoffrey G. Coker, 80 Pickhurst Park, Bromley, Kent, England; John W. A. Findlay, Rte. 2, Box 514, Cascade Dr., Chapel Hill, N.C. 27514

[21] Appl. No.: 635,309

[22] Filed: Jul. 27, 1984

[51] Int. Cl.⁴ .................. C07D 401/06; A61K 31/44
[52] U.S. Cl. .................... 514/343; 514/317; 514/318; 514/423; 546/194; 546/281; 548/532
[58] Field of Search ............. 546/192, 193, 275, 333, 546/194, 227, 281; 544/124, 172; 514/357, 340, 315, 318, 476, 451, 317, 318, 343, 423; 548/532

[56] References Cited

U.S. PATENT DOCUMENTS

| | | | |
|---|---|---|---|
| 2,567,245 | 9/1951 | Sperber et al. | 546/333 |
| 4,562,258 | 12/1985 | Findlay et al. | 546/281 |
| 4,584,382 | 4/1986 | Findlay et al. | 546/314 |

FOREIGN PATENT DOCUMENTS

| | | | |
|---|---|---|---|
| 0081478 | 6/1983 | European Pat. Off. | 546/333 |
| 0085959 | 8/1983 | European Pat. Off. | 546/333 |
| WO8101407 | 5/1981 | European Pat. Off. | 546/333 |
| 2114565A | 8/1983 | United Kingdom | 546/281 |

OTHER PUBLICATIONS

Carren et al., Chemical Abstracts 77:88328m.

*Primary Examiner*—Alan L. Rotman
*Attorney, Agent, or Firm*—Donald Brown

[57] ABSTRACT

The invention provides a compound of the formula (I):

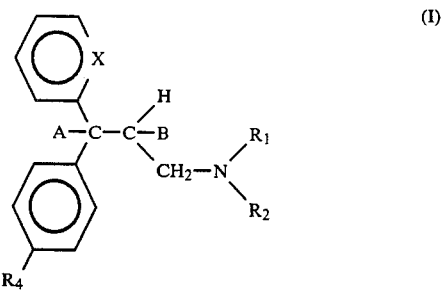

or a salt, ester or amide thereof; wherein $R_1$ is hydrogen or $C_{1-4}$alkyl and $R_2$ is $C_{1-4}$alkyl substituted by a group $R_3CO_2H$ or $R_1$ and $R_2$ taken together with the nitrogen comprise a nitrogen-containing heterocyclic ring having four to six ring members substituted by a group $R_3CO_2H$, wherein $R_3$ is a $C_{1-7}$ aliphatic hydrocarbon group or a single bond;

$R_4$ is hydrogen, halogen, hydroxy, cyano, $C_{1-4}$acyloxy, $C_{1-4}$alkoxy or $C_{1-4}$alkyl optionally substituted by one to three halogen atoms;

X is $-N=$ or $-CH=$; and

A and B each represent hydrogen atoms or $-CA-CB-$ represents $-C=C-$.

The invention also provides a method for the preparation of compounds of the formula (I), novel chemical intermediates in their preparation and pharmaceutical formulations. Compounds of the formula (I) have antihistaminic activity.

4 Claims, No Drawings

CERTAIN 1,1-DIARYL-PROPENYL-3-(1-PYRROLIDINO-2-CARBOXYLIC ACIDS, DERIVATIVES THEREOF AND THEIR ANTI-HISTAMINIC PROPERTIES

The present invention relates to new chemical compounds exhibiting antihistamine activity, to processes for preparing them, to novel intermediates involved in their preparation, to pharmaceutical compositions containing them and to their use in medicine.

U.S. Pat. No. 2,567,245 discloses a group of pyridyl aliphatic amines with antihistamine activity and specifically discloses 3-(p-bromophenyl)-3-(2-pyridyl)-N,N-dimethylpropylamine and 3-(p-chlorophenyl)-3-(2-pyridyl)-N,N-dimethylpropyl-amine which are hereinafter referred to by their generic names brompheniramine and chlorpheniramine respectively.

U.S. Pat. No. 2,717,023 discloses a group of pyridyl propenylamines with antihistamine activity, the most outstanding of which is the compound named (E)-1-(4-methylphenyl)-1-(2-pyridyl)-3-pyrrolidinoprop-1-ene and hereinafter referred to by its generic name, triprolidine. Triprolidine has gained widespread clinical acceptance and is one of the most potent antihistamines available.

Triprolidine is known to be metabolized in man to (E)-1-(4-carboxyphenyl)-1-(2-pyridyl)-3-pyrrolidino-prop-1-ene which has little or no antihistamine activity.

The antihistamines now in use, including diphenylhydramine, the pheniramines, pyrilamine, promethazine and triprolidine have one potential disadvantage in common; they all cause sedation or drowsiness in some patients.

A novel group of compounds having antihistamine activity has now been discovered.

Accordingly this invention provides a compound of the formula (I).

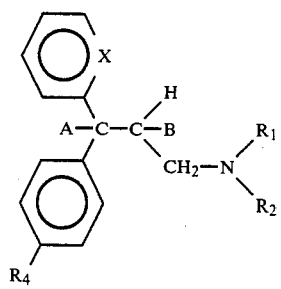

(I)

or a salt, ester or amide thereof; wherein $R_1$ is hydrogen or $C_{1-4}$ alkyl and $R_2$ is $C_{1-4}$ alkyl substituted by a group $R_3CO_2H$ or $R_1$ or $R_2$ taken together with the nitrogen comprise a nitrogen-containing heterocyclic ring having four to six ring members substituted by a group $R_3CO_2H$, wherein $R_3$ is a $C_{1-7}$ aliphatic hydrocarbon group or a single bond;
$R_4$ is hydrogen, halogen, hydroxy, cyano, $C_{1-4}$ acyloxy, $C_{1-4}$ alkoxy or $C_{1-4}$ alkyl optionally substituted by one to three halogen atoms;
X is $-N=$ or $-CH=$; and
A and B each represent hydrogen atoms or $-CA-CB-$ represents $-C=C-$.

Suitably $R_1$ is a methyl or ethyl group. Suitably $R_2$ is a methyl or ethyl group substituted by a group $R_3CO_2H$, or $NR_1R_2$ form a four to six-membered hetero cyclic ring, preferably a saturated heterocyclic ring such as pyrrolidine, piperidine or morpholine, substituted by a group $R_3CO_2H$. When $NR_1R_2$ is a heterocyclic ring the group $R_3CO_2H$ is preferably attached to the carbon atom adjacent to the nitrogen atom which acts as a link between the heterocyclic group and the rest of the molecule. Preferably $NR_1R_2$ is a dimethylamino group or a pyrrolidine group substituted by a group $R_3CO_2H$.

$R_3$ may be a straight or branched chain, saturated or unsaturated hydrocarbon group or a single bond. Suitably $R_3$ is a straight chain $C_{1-4}$ hydrocarbon group or a single bond. Suitably $R_3$ contains at the most one double or triple bond. Preferably $R_3$ is a group $(CH_2)_n$ wherein n is an integer 0 to 4, or a group $(CH_2)_a CH=CH(CH_2)_b$ where a and b are independently 0 to 3 and the sum of a and b does not exceed 3. Most preferably $R_3$ is a single bond.

Suitably n is 0 to 3 and preferably n is 2. Suitably the sum of a and b does not exceed 2 and preferably a and b are both 0.

Suitably $R_4$ is hydrogen, halogen, $C_{1-4}$ alkyl, $C_{1-4}$ alkoxy or trifluoromethyl. Most suitably $R_4$ is hydrogen, methyl, ethyl, trifluoromethyl, methoxy, bromo, chloro or fluoro. Preferably $R_4$ is methyl, trifluoromethyl, methoxy, bromo or chloro. Most preferably $R_4$ is methyl.

Preferably X is $-N=$.

A preferred group of compounds of the formula (I) is that of the formula (II):

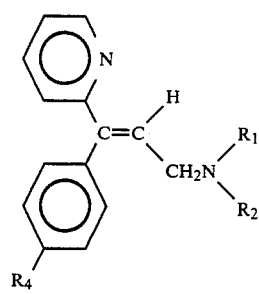

(II)

or a salt, ester or amide thereof; wherein $R_1$ to $R_4$ are as hereinbefore defined. Of the compounds of the formula (II), those wherein $NR_1R_2$ is pyrrolidino substituted by $CO_2H$, $CH=CHCO_2H$ or $CH_2CH_2CO_2H$ and $R_4$ is methyl or trifluoromethyl are particularly preferred.

A further preferred group of compounds of the formula (I) is that of the formula (III)

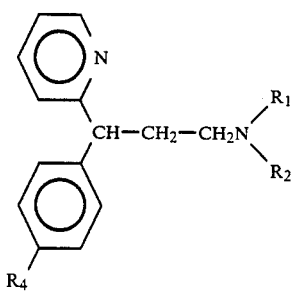

(III)

or a salt, ester or amide thereof; wherein $R_1$ to $R_4$ are as hereinbefore defined. Of the compounds of the formula (III), those wherein $NR_1R_2$ is dimethylamino or pyrrolidino substituted by $CO_2H$, $CH=CHCO_2H$ or CH$_2$CH$_2$CO$_2$H and R$_4$ is chlorine or bromine are particularly preferred.

Amides of the compounds of the formula (I) included within the scope of the invention are amides conventionally formed from carboxylic acids. Amides formed from ammonia, primary amines or amino acids, such as glycine, are particularly suitable.

Solvates of the compounds of the formula (I) are also included within the scope of the present invention. Preferred solvates include hydrates and C$_{1-4}$ alkanolates.

When the compounds of formula (I) contain a double bond in the side chain terminating in the group NR$_1$R$_2$, for example the compounds of formula (II), they exist in either the cis or trans isomeric form(s) (in relation to the X-containing ring). The compounds of the formula (II) have been drawn in the trans configuration and these are the isomers which primarily have useful antihistamine activity. The compounds in the cis configuration are primarily useful as intermediates in preparing the trans isomers. The present invention also provides mixtures of the isomers. When R$_3$ in the substituent R$_3$CO$_2$H contains a double bond, further isomers of the compounds of the formula (I) exist, and bond isomers and the isomeric mixture of these compounds are included within the scope of the present invention.

Esters and amides of the compounds of the formula (I) whilst having some antihistamine activity in their own right may also be useful intermediates in the preparation of the carboxy compounds of the formula (I). Suitable esters include conventional ester groups known to be useful for protecting carboxylic acid groups such as C$_{1-6}$ alkyl esters wherein the alkyl group is straight or branched chain and is optionally substituted by halogen. Alkyl esters (C$_{1-4}$) are particularly preferred.

Salts of the compounds of formula (I) may be either acid addition salts or salts formed with the carboxylic acid group. Acid addition salts are preferred but salts formed from the carboxylic acid group may be particularly useful in preparing the corresponding carboxy compound. Pharmaceutically acceptable salts are preferred.

When used in medicine, the salts of the compound of formula (I) should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable acid addition salts include, but are not limited to, those prepared from the following acids: hydrochloric, sulphuric, nitric, phosphoric, maleic, salicyclic, toluene-p-sulphonic, tartaric, citric, methanesulphonic, formic, malonic, isethionic, succinic, naphthalene-2-sulphonic and benzenesulphonic. Also, pharmaceutically acceptable salts can be prepared as alkaline metal or alkaline earth salts, such as sodium, potassium or calcium salts of the carboxylic acid group.

Preferred compounds of the formula (I) include:
1-(3-(2-pyridyl)-3-(4-tolyl)prop-2E-enyl)pyrrolidine-2-carboxylic acid
or salts, esters, solvates or amides thereof.

The present invention also provides a method for preparing compounds of the formula (I), which method comprises:
(a) The reaction of a compound of the formula (IV)

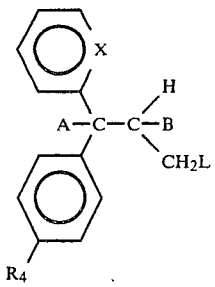

(IV)

or an ester thereof with an amine HNR$_1$R$_2$ wherein X, A, B and R$_1$ to R$_4$ are as hereinbefore defined and L is a leaving group;

(b) When it is required to prepare a compound of the formula (I) wherein CA—CB represents a double bond:
(1) The reaction of a compound of the formula (V):

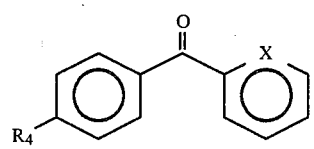

(V)

with a Wittig reagent suitable for attaching the side chain =CHCH$_2$NR$^1$R$^2$ wherein X and R$_1$ to R$_4$ are as hereinbefore defined and the carboxylic acid group is in the form of an ester, amide or salt, followed by deprotection of the carboxy group if desired;

(2) The elimination of R$^5$OH from a compound of the formula (VI):

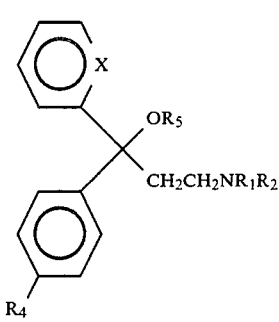

(VI)

or an ester or amide thereof, wherein X, R$_1$ to R$_4$ are as hereinbefore defined and R$^5$ is hydrogen or C$_{1-4}$ acyl;

(3) The reaction of a compound of the formula (VII):

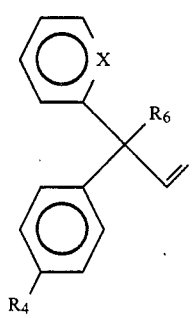

(VII)

with an amine HNR$_1$R$_2$, wherein R$_1$ to R$_4$ are as hereinbefore defined and R$_6$ is a C$_{1-4}$ acyloxy group;

(c) and thereafter, optionally converting one compound of the formula (I) to another compound of the formula (I) by methods well known to those skilled in the art, for example the isomerisation of a compound of the formula (VIII)

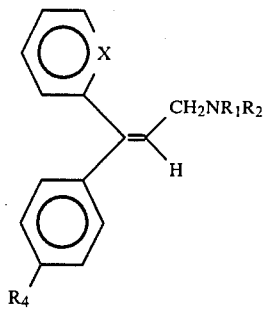

(VIII)

when CA—CB is a double bond, the reduction of one or more double bonds or de-esterification of the ester group.

(a) Suitable leaving groups L in the compounds of the formula (IV) are those as defined by J. March, *Advanced Organic Chemistry*, 2nd ed., pages 683 and 895, McGraw Hill, New York, 1977, e.g. —Br, —Cl, toluenesulphonate, methanesulphonate, acyloxy (such as acetate), etc.

This reaction will normally be carried out in a solvent suitable for carrying out such displacement reactions, for example a polar solvent, such as C$_{1-4}$ alkanol or a polar aprotic solvent such as dimethyl sulphoxide, at a temperature between 0° and 180° C.

The compounds of the formula (IV) may be prepared by the reaction of the corresponding compound where L is a hydroxy group with an acid or a suitable reactive acid derivative. Suitable reactants include hydrogen halides, halogenated phosphorus compounds such as phosphorus pentachloride or phosphorus oxychloride, a suitable sulphonyl chloride (such as methane sulphonyl chloride or p-toluene sulphonyl chloride) or an acid anhydride, such as acetic anhydride. The reaction will conveniently be carried out in a suitable solvent under conditions well known to those skilled in the art, for example a non-protic solvent such as an ether or a halogenated hydrocarbon, in the present of a base such as a tertiary amine (for example triethylamine) at a non-extreme temperature, for example between 0° and 100° C. and conveniently at room temperature. When a tertiary amine is used as a base, an excess of this may be used as the solvent.

The hydroxy compounds wherein —CA—CB— represents —C═C— may be prepared by the reaction of a compound of formula (V) with an appropriate Wittig reagent containing a protected hydroxy group for example

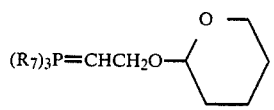

wherein R$^7$ is a C$_{1-4}$ alkyl or phenyl group, which is liberated by the action of strong base on the corresponding phosphonium salt

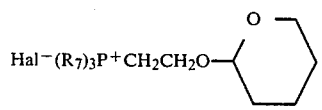

where Hal is chlorine or bromine, followed by deprotection of the hydroxy group in a conventional manner, for example mild acid hydrolysis.

The compounds of the formula (IV) wherein —CA—CB— represents —C═C— may also be prepared by the rearrangement of a compound of the formula (VII). This rearrangement is suitably carried out in the presence of a catalyst, for example a suitable solubilised palladium catalyst, such as bis-(benzonitrile)-palladium (II) dichloride or bis-(acetonitrile)palladium (II) dichloride, in a suitable solvent, preferably in a suitable polar aprotic solvent, such as acetonitrile, at a non-extreme temperature, for example between 20° and 120° C., most suitably between 40° and 90° C., followed by conversion of the group R$_6$ to a leaving group L by conventional methods, normally via the compound where L is a hydroxy group. The corresponding compounds wherein —CA—CB— represents —CH—CH— may be prepared from the unsaturated compounds by reduction, for example hydrogenolysis in the presence of a suitable transition metal catalyst, such as palladium on charcoal.

(b(i)) The Wittig reagent is conveniently a compound of the formula (R$_7$)$_3$P═CHCH$_2$NR$_1$R$_2$ which can be liberated from its corresponding phosphonium salt (R$_7$)$_3$P$^+$CH$_2$CH$_2$NR$_1$R$_2$ Hal$^-$ wherein Hal,R$_1$ and R$_2$ are as hereinbefore defined and R$_7$ is a C$_{1-4}$ alkyl or phenyl group by reaction with a strong base. The reaction is suitably carried out in an inert solvent such as toluene or tetrahydrofuran at a temperature of between 0° and 50° C. and conveniently at room temperature. Suitably the strong base is an alkyl or aryl lithium compound, such as butyl lithium, or a metal hydride, such as sodium hydride. The use of butyl lithium in toluene at room temperature has been found to be particularly convenient. The phosphonium salts (R$_7$)$_3$P$^+$CH$_2$BR$_1$R$_2$ Hal$^-$ may be prepared by known methods (see, for example, U.K. Pat. No. 1161201).

The compounds of formula (V) can be prepared by treatment of a compound of formula (IX) with a metal alkyl compound, for example butyllithium, in suitable solvent such as toluene, followed by reaction with a compound of formula (X) wherein R$_8$ is halogen such as chlorine or bromine and R$_4$ is a hereinbefore defined.

(IX)

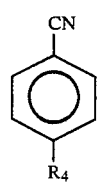

(X)

(b(2)) The elimination of R$_5$ OH from compounds of furmula (VI) is conveniently accomplished in the presence of a strong mineral acid, for example concentrated sulphuric acid, at an elevated temperature, for example between 100° and 200° C., suitably 125° to 150° C.

The compound of the formula (VI) is conveniently prepared from the reaction of a compound of formula (IX) with a metal alkyl compound such as butyllithium followed by reaction with a compound of the formula (XI):

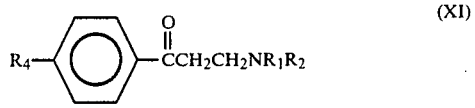

This reaction is suitably carried out at low temperature, for example between −90° and −30° C., conveniently between −70° and 40° C., in an inert solvent, for example toluene, and in inert atmosphere.

This reaction is suitably carried out at low temperature, for example between −90° and −30° C., conveniently between −70° and −40° C., in an inert solvent, for example toluene, and in an inert atmosphere.

(b(3)) The reaction of a compound of formula (VII) with an amine $HNR_1R_2$ is suitably carried out in the presence of a palladium catalyst. The reaction is conveniently carried out in a polar aprotic solvent, such as acetonitrile, at an elevated temperature, for example between 20° and 100° C., suitably between 30° and 80° C. and conveniently between 50° and 70° C. This reaction is conveniently carried out on an ester of the amine $HNR_1R_2$.

The compounds of formula (VII) may conveniently be prepared by the acylation of the corresponding compound wherein $R_6$ is a hydroxy group. This reaction is suitably carried out by the use of the appropriate acyl anhydride in the presence of base, for example triethylamine. The use of 4-N,N-dimethylaminopyridine as a catalyst has been found to facilitate this reaction. The preparation of the hydroxy compounds is suitably carried out by the reaction of a compound of the formula (V) with a Grignard reagent $CH_2=CHMg$ Hal wherein Hal is a suitable halogen atom such as bromine. This reaction is carried out under conditions conveniently used for Grignard reactions, for example in an inert anhydrous solvent such as tetrahydrofuran and can advantageously be carried out in the presence of zinc chloride thereby generating divinyl zinc which reacts with the compound of the formula (V) in situ.

(c) The isomerization of a compound of the formula (VIII) is suitably carried out in the presence of in excess of one molar equivalent of a strong acid, suitably a strong mineral acid, for example sulphuric acid, at an elevated temperature, for example between 50° and 160° C., conveniently between 125° and 150° C.

The compounds of the formula (VIII) may be prepared as by-products in some of the reaction methods for the preparation of compounds of the formula (I) and may be obtained from the reaction mixture by conventional separation techniques, for example by chromatography or by techniques that rely on solubility differences between the two isomers in a suitable solvent.

The reduction of one or two double bonds, i.e. the reduction of the double bond terminating in the group $NR_1R_2$ or the reduction of the double bond in the carboxy side chain may conveniently be carried out by hydrogenation in the presence of a transition metal catalyst, for example palladium on charcoal. The preparation of esters or amides from the corresponding carboxylic acid, and vice versa, may similarly be carried out by methods well known to those skilled in the art.

Those intermediates of the formulae (IV), (VI), (VII) and (XI) that are novel form an important further aspect of the present invention.

The compounds of this invention may be used for the same indications as triprolidine, namely to relieve symptoms of nasal stuffiness due to colds and vasomotor rhinitis and for the symptomatic control of allergic conditions including nasal allergy, perennial rhinitis, urticaria, angioneurotic oedema, allergic conjunctivitis, food allergy, drug and serum reactions, insect bites and stings and desensitizing reactions. The compounds may also be used in conditions responsive to their antipruritic activity including allergic dermatoses, neurodermatitis, anogenital pruritus, and pruritus of non-specific origin such as eczema, and of specific cause such as chickenpox, photosensitivity and sunburn. The present invention therefore provides a method for the symptomatic treatment of allergic conditions by the administration of an effective amount of a compound of the formula (I). The present invention also provides a method for the antagonism of endogenously released histamine by the administration of an effective amount of a compound of the formula (I). Some of the compounds of the present invention have been found to be substantially free from sedative effects and to have little or no anticholinergic effects.

The amount of active compound required for use in the above conditions will vary with the compound chosen, the route of administration and the condition and mammal undergoing treatment, and is ultimately at the discretion of the physician. A suitable oral dose of the active compound for a mammal is in the range of from 0.003 to 1.0 mg per kilogram body weight per day; preferably from 0.04 to 0.24 mg/kg. For example a typical dose for a human recipient of compound (A) (see example 1 and Table 1 hereafter) is 0.12 mg/kg body weight per day.

The desred daily dose is preferably presented as from one to six sub-doses administered at appropriate intervals throughout the day as needed. Where three sub-doses of compounds of formula (I) are employed, each will preferably lie in the range of from 0.014 to 0.08 mg/kg body weight; for example, a typical sub-dose of such a compound for a human recipient is between 1 and 20 mg, for example 4 or 8 mg.

Whilst it is possible for a compound of the formula (I) to be administered alone as the raw chemical, it is preferable to present the compound of formula (I) as a pharmaceutical formulation. Thus, the present invention also provides pharmaceutical formulations, both for veterinary and for human medical use, which comprise a compound of the formula (I) together with one or more pharmaceutically acceptable carriers thereof and optionally any other therapeutic ingredients. For example, the active compound may be formulated with a sympathomimetic agent such as the decongestant pseudoephedrine, an antitussive such as codeine, an analgesic, an antiinflammatory, an antipyretic, or an expectorant. The carrier(s) must be pharmaceutically acceptable in the sense of being compatible with the other ingredients of the formulation and not deleterious to the recipient thereof.

The formulations include those suitable for oral, rectal, topical, nasal, ophthalmic or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound (defined herein as a compound of formula (I)); as a powder or granules; or a suspension in an aqueous liquid or nonaqueous liquid such as a syrup, and elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with any suitable carrier may be made by molding in a suitable machine.

A syrup may be made by adding the active compound to a concentrated, aqueous solution of a sugar for example sucrose to which may also be added any accessory ingredient(s). Such accessory ingredient(s) may include flavourings, an agent to retard crystallization of the sugar or an agent to increase the solubility of any other ingredient, such as a polyhydric alcohol, for example glycerol or sorbitol, and suitable preservatives.

Formulations for rectal administration may be presented as a suppository with a usual carrier such as cocoa butter, or hydrogenated fats or hydrogenated fatty carboxylic acids.

Formulations suitable for parenteral administration conveniently comprise a sterile aqueous preparation of the active compound which is preferably isotonic with the blood of the recipient.

Nasal spray formulations comprise purified aqueous solutions of the active compound with preservative agents and isotonic agents. Such formulations are adjusted to a pH and isotonic state compatible with the nasal mucous membranes.

Ophthalmic formulations are prepared by a similar method to the nasal spray except that the pH and isotonic factors are adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavouring agents, binders, disintegrants, surface active agents, thickeners, lubricants, preservatives (including antioxidants) and the like.

The present invention also provides the first use of the compounds of the formula (I) in medicine.

The following Examples are provided by the way of illustration of the present invention and should in no way be construed as a limitation thereof. All temperatures indicated are in degrees Celsius.

EXAMPLE 1

1-[3-(2-pyridyl)-3-(4-tolyl)prop-2E-enyl]pyrrolidine-2-carboxylic acid monohydrate L-Proline ethyl ester (20 g) was added to a stirred suspension of 2-phenoxyethyltriphenylphosphonium bromide (35 g) in ethanol (70 ml). Gentle warming gave a clear solution. After 20 hours ether was added to precipitate 2-(2-ethoxycarbonylpyrrolidino)ethyl-triphenylphosphonium bromide as colourless prisms, m.p. 181°-2°. (26 g).

A mixture of the above phosphonium salt (11.6 g) with 2-(4-toluoyl)pyridine (4.5 g) in dry tetrahydrofuran (100 ml). was treated at 0° under nitrogen with sodium hydride (1.1 g). After stirring at room temperature for 7 hours the ice-bath was re-applied. Hydrochloric acid (50 ml), 2M) was cautiously added followed by ether (50 ml). The aqueous phase was separated, washed with ether, basified with ammonia (ice) and thoroughly extracted with light petroleum (Bp 40°-60°). Evaporation of the dried extracts gave a yellow oil (1.65 g) consisting of 2 parts of Z to 1 part of E olefin (NMR spectrum). Sulphuric acid (3.5 ml, 95%) was added and the resulting solution was heated at 130° for 1 hour. Re-esterification and re-isolation gave a golden oil (0.65 g) in which the double bond was now mainly in the E configuration. The acid obtained by saponification was purified by treatment with activated charcoal in acetone solution. Evaporation afforded a cream-coloured amorphous solid having analytical and spectral data consistent with the structure of the title compound. gave (E)-3-$\mu$6-$\gamma$3-pyrrolidino-1-(4-tolyl)prop-1E-enyl$\simeq$2-pyridyl$\pm$acrylic acid as off-white crystals, m.p. 218-9$\alpha$ (decomp.). A further recrystallization from isopropanol raised the melting point to 222-3$\alpha$.

EXAMPLE 2

Antihistaminic Activity

A. Invitro antihistaminic activity: The longitudinal muscle was isolated from the intact ileum of guinea-pigs (Hartley, male 250-400 g) and placed in an organ bath under 300 mg tension. After one hour of equilibration, cumulative concentration-response curves (Van Rossum, J. M., Arch. Int. Pharmacodyn. Ther. 143 299-330, 1963) to histamine were obtained. Following washing, the tissues were incubated for one hour with the test compound and then a second histamine concentration-response curve was run. Shifts to the right of the agonist concentration-response curve produced by the antagonists were used to construct Schild plots (Arunlakshana, O. and Schild, H. O., Br. J. Pharmacol: 14, 48-58, 1959). Regression of Log (dr-1) on Log|B|, where dr is an equiactive response in the presence and absence of antagonist and |B| is the molar concentration of antagonist, allowed an estimate of $pA_2$, i.e. the negative log of the concentration of antagonist which shifts the control histamine concentration-responsive curve 2X to the right. 1-(3-

(2-pyridyl 4)3-(4-tolyl)prop-2E-enyl)pyrrolidine-2-carboxylic acid monohydrate had a $pA_2$ of 6.6.

EXAMPLE 3

Formulations

| (A)-Injection | |
|---|---|
| Ingredient | Amount per ampoule |
| Compound of formula (I) | 1.0 mg |
| Water for Injections, q.s. | 1.0 mL |

The finely ground active compound was dissolved in the water for Injections. The solution was filtered and sterilized by autoclaving.

| Ingredient | Amount per suppository |
|---|---|
| Compound of Formula (I) | 1.0 mg |
| Cocoa Butter, or Wecobee ™ Base q.s. | 2.0 g |

Wecobee is a trademark and is a hydrogenated fatty carboxylic acid.

The finely ground active compound was mixed with the melted suppository base (either Cocoa Butter or Wecobee ™ base), poured into molds and allowed to cool to afford the desired suppositories.

| (C)-Syrup | |
|---|---|
| Ingredient | Amount per 5 mL |
| Compound of Formula (I) | 1.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Coloring | q.s. |
| Water | q.s. to 5.0 mL |

Ethanol, sucrose, sodium benzoate, methylparaben, and flavouring were combined in 70% of the total batch quantity of water. Coloring and the active compound were dissolved in the remaining water, then the two solutions were mixed and clarified by filtration.

| (D)-Tablet | |
|---|---|
| Ingredient | Amount per Tablet |
| Compound of Formula (I) | 1.0 mg |
| Lactose | 110.0 mg |
| Corn Starch, Pregelatinized | 2.5 mg |
| Potato Starch | 12.0 mg |
| Magnesium stearate | 0.5 mg |

The active compound was finely ground and intimately mixed with the powdered excipients lactose, corn starch, potato starch and magnesium stearate. The formulation was then compressed to afford a tablet weighing 126 mg.

| (E)-Capsule | |
|---|---|
| Ingredient | Amount per Capsule |
| Compound of Formula (I) | 1.0 mg |
| Lactose | 440.0 mg |
| Magnesium Stearate | 5.0 |

The finely ground active compound was mixed with the powdered excipients lactose, corn starch and stearic acid and packed into gelatin capsules.

| (F)-Tablet | |
|---|---|
| Ingredient | Amount per Tablet |
| Compound of Formula (I) | 1.0 mg |
| Pseudoephedrine HCl | 60.0 mg |
| Lactose | 62.5 mg |
| Potato Starch | 14.0 mg |
| Magnesium Stearate | 1.0 mg |
| Gelatin | 2.8 mg |

A tablet was prepared from the above formulation by the method previously described in Example 3(D).

| (G)-Syrup | |
|---|---|
| Ingredient | Amount per 5 mL |
| Compound of Formula (I) | 1.0 mg |
| Pseudoephedrine HCl | 30.0 mg |
| Codeine Phosphate | 10.0 mg |
| Guaifenesin | 100 mg |
| Methylparaben | 0.5 mg |
| Sodium benzoate | 0.5 mg |
| Flavor q.s. | |
| Color q.s. | |
| Glycerol | 500 mg |
| Sucrose | 2000 mg |
| Purified Water q.s. to | 5.0 mL |

A syrup containing other active ingredients in addition to a compound of formula (I) was prepared from the above ingredients by an analogous method to that described for Example 3(C) above.

| (H)-Nasal Spray | |
|---|---|
| Ingredient | Amount per 100.0 mL |
| Compound of Formula (I) | 1 g |
| Sodium Chloride | 0.8 g |
| Preservative | 0.5 g |
| Purified Water q.s. | 100.0 mL |

The preservative was dissolved in warm purified water and after cooling to 25°–30° C. the sodium chloride and the compound of formula (I) were added. The pH was then adjusted to 5.5–6.5 and purified water was added to bring the final volume to 100.0 mL.

| (I)-Ophthalmic.Solution | |
|---|---|
| Ingredient | Amount per 100.0 mL |
| Compound of Formula (I) | 0.1 g |
| Sodium Chloride | 0.8 g |
| Preservative | 0.5 g |
| Water for Injection q.s. | 100.0 mL |

This formulation was prepared in a similar way to the nasal spray.

| (J)-Topical Cream | |
|---|---|
| Ingredient | Amount per 100.0 mL |
| Compound of Formula (I) | 0.1 g |
| Emulsifying Wax, N.F. | 15.0 g |
| Mineral Oil | 5.0 g |
| White Petrolatum | 5.0 g |
| Preservative | 0.25 g |

We claim:

1. A compound of the formula (I):

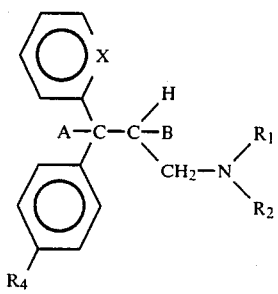

or a pharmaceutically acceptable salt or $C_{1-4}$ alkyl ester thereof; wherein $R_1$ and $R_2$ taken together with the nitrogen to which they are attached form a saturated a heterocyclic ring containing one nitrogen atom and four or five carbon atoms with said ring substituted with the group $R_3CO_2H$ at 2-position wherein $R_3$ is a single bond; $R_4$ is hydrogen, halogen, hydroxy or $C_{1-4}$ alkyl optionally substituted by one or three halogen atoms; X is —N= or —CH=; and —CA—CB— represents —C=C—.

2. 1-(3-(2-pyridyl)-3-(4-tolyl)prop-2E-enyl)pyrrolidine-2-carboxylic acid or a pharmaceutically acceptable salt or $C_{1-4}$ alkyl ester thereof.

3. A method of providing an antihistaminic effect in a human in need thereof comprising administering an effective antihistaminic amount of the compound of claim 1 to said human.

4. A method of providing an anithistaminic effect in a human in need thereof comprising administering an effective antihistaminic amount of the compound of claim 2 to said human.

* * * * *